United States Patent [19]
Schultz et al.

[11] Patent Number: 5,783,175
[45] Date of Patent: Jul. 21, 1998

[54] DUST-FREE HAIR BLEACH POWDERS

[75] Inventors: Thomas M. Schultz, Randolph; Michael DeGeorge, Toms River, both of N.J.; David Cannell, New York, N.Y.

[73] Assignee: Cosmair, Inc., New York, N.Y.

[21] Appl. No.: 817,959

[22] PCT Filed: Aug. 27, 1996

[86] PCT No.: PCT/US96/13764

§ 371 Date: Apr. 29, 1997

§ 102(e) Date: Apr. 29, 1997

[87] PCT Pub. No.: WO97/07776

PCT Pub. Date: Mar. 6, 1997

Related U.S. Application Data

[63] Continuation-in-part of Ser. No. 521,192, Aug. 30, 1995.

[51] Int. Cl.⁶ .................. A61K 7/07; A61K 7/075; A61K 7/135
[52] U.S. Cl. .................. 424/62; 424/70.1; 424/DIG. 3; 424/489; 514/772.4; 132/208; 8/101; 8/111
[58] Field of Search .................. 424/62, 70.1, DIG. 3, 424/489; 132/208; 8/101, 111; 514/772.4

[56] References Cited

U.S. PATENT DOCUMENTS

| | | | |
|---|---|---|---|
| Re. 33,786 | 1/1992 | Pohl et al. | 8/406 |
| 3,726,967 | 4/1973 | Vorsatz et al. | 424/62 |
| 3,975,515 | 8/1976 | Wajaroff et al. | 424/72 |
| 4,170,637 | 10/1979 | Pum | 424/62 |
| 4,507,278 | 3/1985 | DeMarco et al. | |
| 4,552,679 | 11/1985 | Schobel et al. | |
| 4,663,158 | 5/1987 | Wolfram et al. | 424/70 |
| 4,671,972 | 6/1987 | Schobel et al. | 427/213 |
| 5,293,885 | 3/1994 | Darkwa et al. | |
| 5,427,588 | 6/1995 | Lagrange et al. | 8/423 |
| 5,447,654 | 9/1995 | Millequant et al. | |
| 5,458,871 | 10/1995 | Malawer et al. | 424/47 |

FOREIGN PATENT DOCUMENTS

| | | |
|---|---|---|
| 0253772 | 1/1988 | European Pat. Off. |
| 0560088 | 9/1993 | European Pat. Off. |
| 0574696 | 12/1993 | European Pat. Off. |
| 0583767 | 2/1994 | European Pat. Off. |
| 0630643 | 12/1994 | European Pat. Off. |
| 0672408 | 9/1995 | European Pat. Off. |

*Primary Examiner*—Gollamudi S. Kishore
*Assistant Examiner*—Brian K. Seidleck
*Attorney, Agent, or Firm*—Baker & Botts, L.L.P.

[57] ABSTRACT

The invention relates to substantially dust-free bleach powders that, when mixed with aqueous hydrogen peroxide, yield activated bleach compositions that exhibit improved thixotropy. The bleach powders comprise at least one de-dusting agent and at least one peroxygenated salt. The de-dusting agents, which are preferably present in an amount less than about 10% by weight of the bleach powder are inert, substantially hydrophilic compounds selected from alkylated esters, cyclic ethers and cyclic esters. The bleach powders also comprise powdered polytetrafluoroethylene (PTFE) in an amount of about 1–5% by weight of the bleach powder. The bleach powders also comprise an ammonia source, e.g., an ammonium halide, diammonium phosphate, ammonium sulfate and mixtures thereof. Optionally, one or more hair conditioning agents, thickeners and desiccants may be added to the dust-free bleach powder.

31 Claims, No Drawings

DUST-FREE HAIR BLEACH POWDERS

This application is a 371 of PCT/US96/13764, filed Aug. 27, 1996, which is a continuation-in-part of application Ser. No. 521,192, filed Aug. 30, 1995.

BACKGROUND OF THE INVENTION

1. FIELD OF THE INVENTION

The present invention relates to substantially dust-free bleaching formulations. More specifically, the invention is directed to substantially dust-free hair bleaching powders comprising at least one de-dusting agent and at least one peroxygenated salt. The invention also provides hair bleaching powders that, when mixed with aqueous hydrogen peroxide, yield an activated bleaching composition that can flow evenly through hair. More specifically, the bleaching powders of the invention also comprise powdered polytetrafluoroethylene (PTFE), which improves the viscosity and slip characteristics of the activated bleaching composition.

2. Background of the Invention

Conventional hair bleach powders are compositions which are used for lightening hair color. Typically, these products are sold to the consumer as dry powders, which must be mixed with aqueous solutions of hydrogen peroxide before they are used. Upon mixing, the components in the bleach powder and the hydrogen peroxide solution form an activated bleaching composition which is then applied to the hair. The activated bleaching composition lightens the hair by oxidizing natural hair pigments, such as melanin.

Typical hair bleach powders contain a reactant which interacts with hydrogen peroxide to form oxygen, which breaks down melanin in hair. Commonly, such reactants include, inter alia, peroxygenated ammonium, sodium or potassium salts of persulfates, perborates, percarbonates and the like.

It is usually necessary for adequate oxygen formation to have an activated bleach composition with a pH in the range of 9.5–11.5 upon addition of the hydrogen peroxide solution. The peroxide and the persulfate are both acids, which are activated at a basic pH. Accordingly, it is common to add a base, such as an amine alkali compound or a metasilicate, to hair bleach powders.

Conventional hair bleach powders may also contain other additives including thickeners, such as hydroxy-alkylated cellulose, that help form the powder base. Such bleach powders are also susceptible, upon storage, to degradation resulting from atmospheric moisture. Thus, it is also common to add desiccants, such as silica derivatives, to prevent the bleach powders from being degraded by moisture before use.

There are several disadvantages associated with conventional hair bleach powders. Specifically, conventional bleach powders have a tendency to form dust during handling, transport and storage. Dusting also occurs during transfer of the bleach powder to the mixing chamber prior to admixing with the aqueous solution of hydrogen peroxide. Moreover, the persulfates and the alkaline silicate reactants are corrosive, and can be dangerous to the handler. These dusts irritate the eyes, the respiratory canal and the mucous membranes. Ammonium persulfate is an especially problematic irritant.

For these reasons, various attempts have been made to reduce the dusting characteristics of hair bleach powders. Partial success has been achieved through the addition of substantially water insoluble compounds, such as oils or liquid waxes, to the bleach powder. These oils or waxes coat the individual powder particles and agglomerate them into larger sized particles. Such bleach powders are thus rendered substantially dust-free due to their lack of small particles.

Published European Patent Application Publication No. 0583,767 A2, ("EP '767"), provides an example of this approach. EP '767 discloses a dry free flowing, dust-free hair bleach powder, wherein a powder base comprising ammonium, sodium and potassium persulfate salts is treated with "inert adsorbates" or inert liquids which include, inter alia, mineral oils, natural oils and fluorosilicone fluids.

These inert liquid additives, which are oils, are disclosed as performing two functions: (1) as an adhesive to aggregate small powder particles into particles having a size greater than 40µ and (2) as a lubricant to coat the particles so they do not abrade and form dust. Therefore, the inert liquid additives function primarily as de-dusting agents.

In order to obtain the desired characteristics of the compositions taught by EP '767, the inert liquid is said to comprise about 10–25% by weight of the hair bleach powder with the preferred range being about 14–20% by weight.

U.S. Pat. No. 4,170,637 ("'637 patent") also recites a hair bleach composition which comprises an intimate mixture of particulate persulfate salts and alkaline silicates dispersed in a hydrophobic organic carrier, such as an oil or wax, present in an amount from about 30–70% by weight of the total mixture. The resulting compositions are not powders, but have a "paste to cream" consistency.

European Patent Publication No. 0,560,088 B1 ("EP '088") discloses dust-free bleach powders that are also treated with oils and/or liquid waxes. These ingredients comprise from 2.5 to 25%, and preferably between 8 and 12%, of the total weight of the bleach powder. The added substances are also taught as being substantially water-insoluble ("Industrie et technologie des Corps Gras" (Industry and Technology of Fatty Substances), Alton E. Bayley; "Romps Chemie Lexicon", Oho Albrecht and Neumuller; "Introduction to Fats and Oils Technology", Peter J. Wan; Larousse Dictionary). Specifically, EP '088 recites the use of paraffin oil and silicone oil, which are hydrophobic, water insoluble substances.

While the above-recited treatments produce substantially dust-free bleach powders, these powders still suffer from significant drawbacks, because they form unstable oil based emulsions upon mixture with the aqueous hydrogen peroxide. Therefore, to compensate for this instability, additional components, such as surfactants and emulsifiers (e.g., polyoxyethylenestearates or polypropyleneoxides), must be added to the powder. Moreover, when bleach powders containing oil-based de-dusting agents are mixed with aqueous hydrogen peroxide, they take a long time to form a usable paste.

Another undesirable aspect of conventional bleaching compositions is that they fail to exhibit satisfactory thixotropy characteristics. An activated bleaching composition with good thixotropy moves through the hair with little effort, but also remains in the location where it is applied. In other words, good thixotropy properties help the bleach composition recover from sheer forces exerted on it during application to hair. Activated bleaching compositions prepared with the above-mentioned prior art dust-free hair bleach powders do not exhibit good thixotropy, but instead require excessive embrocation or wetting to effectively and evenly bleach the hair. It is difficult to obtain desired thixotropy for an activated bleaching composition, since a moderately low viscosity is required to impart the right amount of spreadability. However, if the viscosity is too low, the prepared bleach paste or cream will not stay in its applied location. Therefore, it is critical for an activated bleaching composition to have an optimum viscosity to impart desirable aesthetic characteristics to the hair.

Conventional bleach powders have further disadvantages in that they decompose under humid conditions and have relatively low ignition temperatures. Moreover, none of the conventional dust-free bleaching powders incorporates substantially hydrophilic de-dusting agents, which simultaneously suppress formation of dust and impart improved thixotropy characteristics to activated bleaching compositions made from these powders. Conventional bleach powders also do not incorporate powdered polytetrafluoroethylene (PTFE), which prevents clumping of the powder when mixed with aqueous peroxide and improves viscosity and slip characteristics of the bleaching mixture.

SUMMARY OF THE INVENTION

Accordingly, it is an object of the invention to provide a substantially dust-free bleaching powder which can be used to prepare an activated bleaching composition that overcomes the disadvantages of the prior art.

Another object of the invention is to provide a substantially dust-free bleaching powder which comprises a substantially hydrophilic de-dusting agent to enhance solubility of the bleach powder in an aqueous peroxide solution.

It is a further object of the invention to provide substantially dust-free bleaching powders that, when mixed with aqueous hydrogen peroxide, form activated bleaching compositions that have improved thixotropy and slip characteristics.

Another object of the invention is to provide a substantially dust-free bleach powder that is less irritating to the user, in which an ammonium halide, ammonium sulfate and a non-ammonia peroxygenated salt are substituted for ammonium persulfate used in conventional.

A further object of the invention is to provide a substantially dust-free bleach powder that incorporates powdered polytetrafluoroethylene (PTFE) to improve the viscosity and slip characteristics of the activated bleaching compositions and to prevent clumping of the powders when mixed with aqueous peroxide.

A still further object of the invention is to provide substantially dust-free bleach powders having conditioning agents which improve the aesthetic feel of the hair.

It is a still another object of the invention to provide substantially dust-free bleach powders that have retarded rates of decomposition under atmospheric humidity.

An additional further object of the invention is to provide substantially dust-free bleaching powders that have high ignition temperatures.

These and other objects of the present invention are achieved by one or more of the following features of the invention.

The objects of the present invention are accomplished through the inclusion of de-dusting agents, that are substantially hydrophilic compounds, and powdered PTFE in the bleach powder. The de-dusting agents are applied to a mixture of the peroxygenated salt and powdered PTFE-containing bleach powder, such that the de-dusting agent coats the bleach powder particles. Preferably, the application of the de-dusting agents is via spraying. This process produces a substantially dust-free bleach powder which can be mixed with an aqueous solution of a peroxide, such as hydrogen peroxide, to form an activated bleaching composition.

In a preferred embodiment of the present invention, the substantially hydrophilic de-dusting agents are cyclic ethers, alkylated diesters or cyclic esters. In a more preferred embodiment, the cyclic ether may be a dialkyl cyclic ether, such as dimethyl isosorbide or diisopropyl isosorbide. The alkylated diester may be an alkylated adipate, alkylated sebecate or alkylated oxalate, wherein the alkyl groups have 3 to 6 carbon atoms. Preferred alkylated diesters include diisopropyl adipate, diisopropyl sebecate, and diisopropyl oxalate. Preferably, the cyclic ester is γ-butyrolactone.

In a further preferred embodiment, the de-dusting agent is present in an amount less than 10% by weight of the bleach powder, preferably 2 to 56 and, more preferably, 2–3%.

The powdered PTFE is present in the bleach powder in an amount of about 1–5% by weight, preferably 2–4% and more preferably about 3%.

In a still further embodiment of the present invention, the peroxygenated salt may be selected from among one or more of the salts of persulfate, perborate, metasilicate, or percarbonate. Sodium and potassium persulfate salts are preferred.

In other preferred embodiments of the invention, several additives such as conditioners, bases, thickeners and desiccants may be added to the powder.

Other features and advantages of the invention will be apparent from the following description of the invention and from the claims.

DETAILED DESCRIPTION OF THE INVENTION

The present invention provides a free flowing, substantially dust-free hair bleach powder that can be mixed with aqueous hydrogen peroxide without clumping to form an activated bleaching composition with improved thixotropy.

The substantially dust-free bleach powders of the invention comprise particles of one or more peroxygenated salts, that are coated with a substantially hydrophilic de-dusting agent. The bleach powders of the invention also comprise powdered polytetrafluoroethylene (PTFE). The substantially dust-free bleach powder may also contain additional components including, inter alia, conditioners, bases, thickeners and desiccants. Before they are used to bleach hair, the substantially dust-free bleach powders must be combined with an aqueous peroxide solution, especially hydrogen peroxide, which forms an activated bleaching composition.

The invention is based, in part, on the finding that substantially hydrophilic cyclic ether compounds, especially dimethyl ethers, cyclic ester compounds, and alkyl diesters are effective de-dusting agents for hair bleaching powders. The invention is further based on the surprising ability of bleaching powders comprising these substantially hydrophilic de-dusting agents to simultaneously suppress formation of dust and impart superior thixotropy characteristics to bleaching compositions made from these powders. The invention is still further based on the improvements to viscosity and slip characteristics of the bleaching powders provided by the inclusion of powdered PTFE therein. The addition of PTFE also reduces clumping of the substantially dust-free bleach powder upon mixing with aqueous peroxide.

Suitable peroxygenated salts for use in the bleaching powders of the invention include salts of persulfate, perborate, metasilicate, or percarbonate. Preferred peroxygenated salts include sodium and/or potassium persulfate.

The de-dusting agents which may be incorporated in the dust-free bleach powder include various substantially hydrophilic agents which enhance miscibility of the powders with aqueous hydrogen peroxide solutions. Preferred de-dusting agents include cyclic ethers, cyclic esters and alkylated diesters. Preferred cyclic ethers include dialkyl cyclic ethers, such as dimethyl isosorbide or diisopropyl isosorbide. Preferred cyclic esters include γ-butyrolactone. Preferred alkylated diesters include alkylated esters wherein the alkyl groups have three to six carbon atoms. More preferred alkylated diesters include dialkyl sebecates, dialkyl oxalates, and dialkyl adipates. Most preferred are diisopropyl sebecate, diisopropyl oxalates and diisopropyl adipates.

The de-dusting agent comprises less than 10% by weight of the total bleach powder. This ensures that the activated bleaching composition made using the powder does not have a cream or paste-like consistency. More preferably the bleach powder comprises about 2–5% and, most preferably, about 2–3% de-dusting agent by weight of the total bleach powder.

The substantially dust-free bleach powders also comprise 1–5%, preferably 2–4% and more preferably 3% cosmetic-grade powdered PTFE by weight. Such powdered PTFE are micropowders (or waxes) known in the art that have a lower molecular weight than that of normal PTFE, while retaining very low solubility. (See *Concise Encyclopedia of Polymer Science and Engineering*, John Wiley & Sons, 1990, pp. 1167–1170, incorporated herein by reference). A preferred PTFE powder is the cosmetic-grade FluoroPURE 103C PTFE powder of Shamrock Technologies, Inc., Newark, N.J. 07114, which has an average particle size of 5µ. Fluoro-PURE 103C is supplied as a white powder, which is preferred for aesthetic reasons. The FluoroPURE powder is usable for powder make-up formulas, providing lubricating properties. Other sources of powdered PTFE include, inter alia, DuPont (Teflone®) and ICI (Fluron), with such PTFE powders having similar particle size and characteristics as the above-mentioned Shamrock product.

The substantially dust-free bleach powders preferably also contain a base including, inter alia, amine alkali compounds such as trishydroxyalkylamines, e.g., trishydroxyethylamine, guanidium carbonate or guanidium borate. Other suitable bases include alkaline silicates, such as sodium silicate or metasilicates, such as sodium metasilicate.

Preferably, ammonium sulfate or an ammonium halide compound, such as ammonium chloride, or diammonium phosphate, or mixtures thereof is utilized as an ammonia source in the present bleach power. Such compounds are preferable to ammonium persulfate used in conventional bleaches as an ammonia source because these compounds impart a lesser odor than ammonium persulfate. Most preferably, the ammonia source is a mixture of ammonium chloride and ammonium sulfate in the dust-free bleach powders comprising PTFE (see Tables 1 and 2).

The substantially dust-free bleach powder of the invention may also contain one or more powdered hair conditioning agents, which can substantially improve the feel of hair treated with the bleaching composition after mixing with hydrogen peroxide. Such conditioning agents include any non-reactive polymeric material known in the art. Preferred conditioning agents include inter alia, anionic, cationic, nonionic or amphoteric conditioners.

Preferred cationic conditioners include, inter alia, polymeric quaternized amine polymers with a molecular weight range of 50 kDa. Specific preferred quaternized amine polymers include MERQUAT 280, made by the Calgon Corporation, also known as Polyquaternium-22, which is a copolymer of dimethyl diallyl ammonium chloride and acrylic acid; Polymer JR, made by the Union Carbide Corporation, also known as Polyquaternium-10, which is a polymeric quaternary ammonium salt of hydroxyethyl cellulose reacted with a trimethyl ammonium substituted epoxide; MERQUAT 2200, also known as Polyquaternium-7, which is a polymeric quaternary ammonium salt consisting of acrylamide and dimethyl diallyl ammonium chloride monomers; and Guar hydroxypropyltrimonium chloride, which is a quaternary ammonium derivative of hydroxypropyl Guar (gum).

Preferred anionic conditioners include, inter alia, sulfonated, carboxylated and nitro-oxide derivatives of cationic polymers, e.g., such as pyrrolidone carboxylic acid (PCA), marketed as Ajdew by the Ajinomoto Company, U.S.A., Inc.

Preferred amphoteric conditioners include chitosan and succinamide.

Preferred nonionic conditioners include monomeric and polymeric compounds such as Poloxamar 407, which is a polyoxyethylene, polyoxypropylene block polymer.

Preferably, the amount of conditioner in the substantially dust-free bleach powder of the invention is about 1%–5% by weight of the bleach powder.

In further preferred embodiments of the invention, thickeners may also be added to the hair bleach powder. Hydroxyethylcellulose is a preferred type of hydroxyalkylated cellulose thickener. In one preferred embodiment, hydroxyethyl cellulose is used in a proportion that is about 3–5% by weight of the total bleach powder. Preferred thickeners also include polymeric methyl vinyl ether/malic anhydride copolymer, cross-linked by 1,9 decadiene ("PVM/MA decadiene crosspolymer").

The substantially dust-free bleach powder may also contain desiccants, such as silica. Preferably, silica is added to the bleach powder in an amount comprising about 1–3% by weight of the total bleach powder.

Surfactants, chelating agents and their salts may also be added to the substantially dust-free bleach powder, in an amount 0.01–2% by weight of the total bleach powder.

A representative substantially dust-free bleach powder according to the present invention may be prepared as shown in Table 1.

TABLE 1

| MATERIAL | WEIGHT PERCENT |
| --- | --- |
| Potassium Persulfate | 30–50 |
| Sodium Silicate | 10–25 |
| Sodium Persulfate | 5–15 |
| Sodium Metasilicate | 5–10 |
| Sodium Stearate | 3–5 |
| Silica | 1–3 |
| Ammonium Chloride | 3–5 |
| Ammonium Sulfate | 1–3 |
| Hydroxyethylcellulose | 3–5 |
| Polytetrafluoroethylene (PTFE) | 1–5 |
| De-dusting solvent | 2–3 |
| Ethylene diamine tetraacetic acid (EDTA) | ~1 |
| Fragrance | ~1 |
| PVM/MA Decadiene Crosspolymer | ~1 |
| Polyquaternium-22 | 1–5 |

Preferably, the de-dusting agent is applied to the bleach powder by a spraying process.

The present invention is further described by way of the following specific examples. These examples are intended to be representative of the invention and are not in any way intended to limit its scope.

EXAMPLE 1

The Substantially Dust-Free Bleach Powders Produce Activated Bleaching Compositions with Superior Thixotropy Properties.

The thixotropy of several activated bleaching compositions was compared. The activated bleaching compositions were made by mixing the bleach powders designated A–G in Table 2 with aqueous $H_2O_2$. Powders A, B and D, upon addition of an oil, i.e., mineral oil, represent prior art commercial products. Powders E and F are powders prepared according to the present invention, that do not contain PTFE. Powder G is a powder of the present invention containing PTFE.

TABLE 2

BLEACH POWDERS

| A | B | C | D | E | F | G | INGREDIENTS |
|---|---|---|---|---|---|---|---|
|   | X | X |   | X | X | X | Ammonium Chloride |
| X |   | X |   |   |   |   | Ammonium Persulfate |
|   |   |   |   |   |   | X | Ammonium Sulfate |
|   | X |   |   |   |   |   | Calcium Stearate |
|   |   |   | X |   |   | X | Diisopropyl Adipate |
|   |   |   |   |   | X |   | Dimethyl Isosorbide |
|   | X |   |   |   |   |   | Dioctyl Sodium Sulfosuccinate |
|   |   | X |   |   |   |   | Disodium EDTA |
|   | X | X |   | X | X | X | EDTA |
| X | X | X | X | X |   | X | Fragrance |
|   | X |   |   |   |   |   | Guar Gum |
|   | X |   |   |   |   |   | Hydrated Silica |
| X | X |   |   | X | X | X | Hydroxyethylcellulose |
|   | X |   |   |   |   |   | Isoeicosane |
|   | X | X |   |   |   |   | Magnesium Carbonate |
|   | X |   |   |   |   |   | Magnesium Oxide |
|   |   | X |   |   |   |   | Methylcellulose |
| X |   |   |   |   |   |   | Pentetic Acid |
|   |   |   | X | X |   | X | Polyquaternium-22 |
|   |   |   |   |   |   | X | Polytetrafluoroethylene (PTFE) |
| X | X | X | X | X | X | X | Potassium Persulfate |
|   |   |   | X |   |   |   | PVP |
| X |   |   | X | X |   |   | PVM/MA/Decadiene Crosspolymer |
|   | X |   |   |   |   |   | PVP/VA Copolymer |
| X | X | X | X | X | X | X | Silica |
|   | X |   |   |   |   |   | Sodium Benzoate |
| X | X | X |   | X | X | X | Sodium Metasilicate |
| X | X | X |   | X | X | X | Sodium Persulfate |
| X |   | X | X | X | X | X | Sodium Silicate |
| X |   | X |   | X | X | X | Sodium Stearate |
|   | X |   |   |   |   |   | Titanium Dioxide |
|   | X |   |   |   |   |   | Ultramarine Blue |

For purposes of comparison, each of the bleach powders was mixed with aqueous hydrogen peroxide to form an activated bleach composition. As shown below, the thixotropy values of each of the activated bleach compositions was evaluated in terms of sheer. Sheer is determined from the ratio of two separately determined viscosity values, obtained by use of a heliopath spindle viscometer made by the Brookfield Company.

Viscosity measurements using the viscometer were obtained at a speed of 2.5 rpm for 30 seconds using two differently sized spindles, designated T-A and T-D. Each of the bleach compositions was placed in a beaker and positioned under the viscometer. The spindles were then placed on the surface of the sample, and their passage through the sample was evaluated for 30 seconds. T-A and T-D values were expressed by the viscometer as Centipoise or cps units. The determined thixotropy values are expressed as the ratio of T-A/T-D. Lower values of T-A/T-D indicate superior thixotropy, that is, the product maintains its viscosity even under the sheer of application. Values >5 indicate that the activated bleach composition will tend to fall apart under sheer. Such mixtures are paste-like, and thus are difficult to apply smoothly and evenly to hair.

Thixotropy values obtained for the different activated bleach compositions are shown in Table 3. The activated bleach compositions prepared using the substantially dust-free bleach powders of the present invention, represented by Powder E (containing an alkyl ester compound, e.g. diisopropyl adipate, see Table 2), and Powder F (containing an cyclic ether compound, e.g. dimethyl isosorbide, see Table 2), each had a T-A/T-D ratio of 0.7. Powder G, which contains powdered PTFE and diisopropyl adipate (see Table 2) had a T-A/T-D ratio of 0.6. These low values for Powders E, F and G indicate a desirable thixotropy. These activated bleach compositions made with Powders E, F and G do not have any added surfactants. In contrast, Powder A (which does not contain any de-dusting agent) when assayed as is, or with 10% w/w mineral oil added, showed T-A/T-D ratios of 5.5 and 5.6, respectively, indicating poor thixotropy. It was necessary to add a surfactant to an admixture of Powder A and 10% mineral oil in order to achieve a desirable thixotropy. See, Table 3.

Therefore, the comparative tests show that bleach compositions made with the substantially dust-free bleach powders of the present invention have superior thixotropy properties compared with conventional bleach powders. Specifically, compositions made with powders E and F exhibited superior thixotropy over compositions prepared with de-dusting agents such as the oils and waxes known in the art.

TABLE 3

| BLEND | T-A Spindle | T-D Spindle | T-A/T-D |
|---|---|---|---|
| Powder A | 196,000 cps | 35,400 cps | 5.5 |
| Powder B | 160,000 cps | 21,000 cps | 7.5 |
| Powder A + 10% W/W Mineral Oil | 180,000 cps | 32,000 cps | 5.6 |
| Powder A + 10% Mineral Oil + 2% W/W Surfactants | 33,600 cps | 29,000 cps | 1.1 |
| Powder C | 40,800 cps | 37,000 cps | 1.1 |
| Powder D | 80,000 cps | 240,000 cps | 0.3 |
| Powder E | 14,800 cps | 20,800 cps | 0.7 |
| Powder F | 20,020 cps | 28,800 cps | 0.7 |
| Powder G | 28,800 cps | 46,800 cps | 0.6 |

EXAMPLE 2

The Substantially Dust-Free Hair Bleach Powders of the Invention are Resistant to Decomposition.

The stability of the bleach powders of the present invention against decomposition was determined by their ability to resist loss of oxygen releasing power. Specifically, experiments were performed to determine the amount of oxygen that is released under conditions of 95% constant humidity within a 3-day period.

The active oxygen in the persulfate component was obtained by calculating the amount of reducible persulfate salt in the bleach powder. This is obtained by reducing the bleach powder with ferrous sulfate, and calculating the amount of excess ferrous sulfate produced in the reaction by titration with potassium permanganate. The amount of reducible persulfate salt is inversely proportional to the amount of excess ferrous sulfate, and can be calculated from the titration values. The percent values of activity represent the fraction of reducible persulfate in the total bleach powder, i.e. an initial activity of ~3% corresponds to the total amount of reducible persulfate salt present in the total bleach powder, i.e., ~3% by weight. The loss of activity is the difference between the amount, in percent, of oxygen released on day 0 and that on day 3.

Table 4 shows the percent of oxygen released from the powders after day 0 and day 3 of exposure to 95% relative humidity. The substantially dust-free bleach powders of the invention, containing either diisopropyl adipate, (Powder E of Table 2) or dimethyl isosorbide, (Powder F of Table 2), showed substantially low loss, i.e. ~0.2%, of activity after a 3-day exposure to 95% constant humidity despite an overall ~33% gain in weight due to absorption of atmospheric moisture.

TABLE 4

|  | POWDER E | POWDER F |
|---|---|---|
| 95% RH/wt gain (3 days) | 33.33% | 33.42% |
| 95% RH/initial activity | 3.18% | 3.15% |
| 95% RH/3 days activity | 2.98% | 2.96% |
| Loss of activity | 0.2% | 0.19% |

RH = relative humidity

EXAMPLE 3

The Substantially Dust-Free Bleach Powders of the Invention have a High Ignition Temperature The effect of the cyclic ether or alkylated ester de-dusting agents on the ignition temperature of the bleach powders was determined. The ignition temperature was obtained by heating the bleach powder on a hot-plate and noting the temperature at which charring occurred. As shown in Table 5, Powder A (of Table 2), which does not contain a de-dusting agent, had an ignition temperature of 170° C. Powder E (containing dimethyl isosorbide) and Powder F (containing diisopropyl adipate) had considerably higher ignition temperatures, e.g., 190° and 195°, respectively. It is an advantage for bleach powders to have high ignition temperatures to eliminate the possibility of fires or explosions during use or transport.

TABLE 5

| Powder | Ignition Temperature °C. |
|---|---|
| A | 170 |
| E | 190 |
| F | 195 |

EXAMPLE 4

Hair Bleached by the Activated Bleach Compositions of the Invention has Superior Combability.

Combability assays performed on hair samples bleached by the activated bleach composition prepared using the substantially dust-free powder bleach of the invention showed reduced resistance of the hair to forces exerted during combing.

The resistance to movement of a comb through the hair was measured in an Instron tensile test using the Instron instrument as known in the art. In this method, pneumatic pressure is applied to pull combs at a given speed through hair swatch samples attached to the Instron. The resistance to movement of the comb is evaluated as (1) the force required to pull the comb through the hair, expressed by the Instron as load at a maximum load, and (2) as the work done by the machine in which the comb is pulled through the hair, expressed by the Instron as energy at break point. Lower resistance indicates superior and desirable Combability.

For the assay, hair swatches were bleached for 45 minutes at room temperature and rinsed thoroughly. They were then dipped in deionized water, and the excess water was gently squeezed out. Then the swatches were slightly detangled with a fine tooth comb and clamped from the top onto the pneumatic air grip of the Instron. Two combs were placed in the Instron opposing one another such that the hair to be tested was evenly distributed between them and the upper comb was 1.5 in. from the lower edges of the clamp. The Instron was set to pull the combs through the swatch and to the end of the swatch, at a speed of 5 in/min. The force and work expended during this time was expressed by the Instron as described above. The final readings were calculated from a mean of ten similar and independent combability assays.

The resistance values obtained for hair bleached by the different activated bleach compositions are shown in Table 6. The resistance values of hair bleached by activated bleach compositions prepared using Powder E and Powder F (containing the de-dusting agents of the invention and a conditioner, e.g., Polyquaternium-22) have a load at maximum load value of 53.73 gms and 36.44 gms, respectively. These values indicate desirable combability. In contrast, activated bleach compositions prepared using Powder D (see Table 2) which does not contain any de-dusting component or a conditioner, has a load at maximum load value of 336.1 gms, indicating undesirable combability.

Similarly, the energy at break point values of hair bleached by activated bleach compositions using Powder E and Powder F are low, i.e., 134.7 gms/in. and 87.02 gms/in., respectively. In contrast, the energy at break point values using the composition containing Powder D is 1306 gms/in. Thus, hair bleached by bleach compositions prepared using Powder E and Powder F, which contain the de-dusting agents of the invention and a conditioner, have substantially superior combability.

TABLE 6

| ACTIVATED BLEACH COMPOSITION | LOAD AT MAX. LOAD (gm) | ENERGY AT BREAK POINT (gm/in.) |
|---|---|---|
| Powder D | 336.1 | 1306 |
| Powder E | 53.73 | 134.7 |
| Powder F | 36.44 | 87.02 |

EXAMPLE 5

Bleach Compositions Prepared with PTFE-Containing Bleach Powder have Superior Properties Salon testing of bleach compositions prepared with Powder G (Table 2) and a prior art bleach, Powder C (Table 2) was carried out in Redken's Testing Laboratories by licensed cosmetologists who are trained in evaluating hair and the effects of bleach compositions on the hair. In particular compositions were tested for off-scalp applicability for use in frosting and foil weaving application.

The test bleach powder (G) and the control bleach powder (C) were each mixed with an emulsion peroxide, Redken's Pro-Oxide 20 volume peroxide. Various parameters, including inter alia, ease of mixing; viscosity; ease of application; rinsability; pre shampoo wet combing, hair condition and shine; post shampoo wet combing, wet feel, hair condition and shine, were compared and graded for the test bleach composition and the control. A grading system of 1–5, with 1 being the poorest value and 5 being the best value was used. The results of the test are set forth in Table 7 below.

TABLE 7

| Measured Parameter | Average | Test Std. Dev. (Powder G) | Confidence Level | Average | Control Std. Dev. (Powder C) | Confidence Level |
|---|---|---|---|---|---|---|
| Mixing Ease | 3.500 | 0.577 | 7.336 | 3.000 | 0.816 | 10.374 |
| Viscosity | 3.500 | 0.577 | 7.336 | 3.250 | 0.500 | 6.353 |
| Ease of Application | 3.500 | 0.577 | 7.336 | 3.250 | 0.500 | 6.353 |
| Puffing in the Bowl | 4.250 | 0.500 | 6.353 | 4.250 | 0.500 | 6.353 |
| Puffing in the foils | 4.250 | 0.957 | 12.165 | 4.750 | 0.500 | 6.353 |
| Rinsability | 3.000 | 0.000 | 0.000 | 3.250 | 0.500 | 6.353 |
| Pre Shampoo Wet Combing | 3.500 | 0.577 | 7.336 | 3.250 | 0.500 | 6.353 |
| Pre Shampoo Hair Condition | 3.250 | 0.500 | 6.353 | 3.000 | 0.000 | 0.000 |
| Pre Shampoo Shine | 3.000 | 0.000 | 0.000 | 3.000 | 0.000 | 0.000 |
| Wet Combing | 4.750 | 0.500 | 6.353 | 4.750 | 0.500 | 6.353 |
| Wet Feel | 3.250 | 0.500 | 6.353 | 3.250 | 0.500 | 6.353 |
| Hair Condition | 3.250 | 0.500 | 6.353 | 3.250 | 0.500 | 6.353 |
| Shine | 3.250 | 0.500 | 6.353 | 3.250 | 0.500 | 6.353 |

As can be seen from Table 7, all measured parameters using the bleach composition made from Powder G were equal to or better than compositions made from Powder C.

Also, the salon results indicated that following a similar application time, superior hair lightening was obtained with Powder G (data not shown).

The above examples are illustrative of the invention and are not meant in any way to limit the scope of the present invention.

We claim:

1. A substantially dust-free bleach powder, which comprises:
  (a) a plurality of particles which comprise a peroxygenated salt,
  (b) a substantially hydrophilic de-dusting agent selected from the group consisting of diisopropyl adipate, diisopropyl sebacate, diisopropyl oxalate dimethyl isosorbide, diisopropyl isosorbide, and γ-butyrolactone in an amount that is less than about 10% by weight of the bleach powder, wherein the de-dusting agent coats the particles to prevent dust formation, and
  (c) powdered polytetrafluoroethylene in an amount of about 1–5% by weight of the bleach powder.

2. The bleach powder according to claim 1 wherein the bleach powder further comprises a base.

3. The bleach powder according to claim 1, wherein the de-dusting agent is present in an amount of about 2 to 5% by weight of the bleach powder.

4. The bleach powder according to claim 1, wherein the de-dusting agent is present in an amount of about 2–3% by weight of the bleach powder.

5. The bleach powder according to claim 1, wherein the polytetrafluoroethylene is present in an amount of about 2–4% by weight of the bleach powder.

6. The bleach powder according to claim 1, wherein the powdered polytetrafluoroethylene is present in an amount of about 3% by weight of the bleach powder.

7. The bleach powder according to claim 1, wherein the peroxygenated salt is selected from the group consisting of water soluble salts of persulfates, percarbonates, perborates, and metasilicates.

8. The bleach powder according to claim 7 wherein the peroxygenated salt is selected from the group consisting of sodium persulfate and potassium persulfate.

9. The bleach powder according to claim 2, wherein the base is selected from the group consisting of amine alkali compounds, alkaline silicates and alkaline metasilicates.

10. The bleach powder according to claim 9, wherein the amine alkali is selected from the group consisting of trishydroxyalkylamines, guanidinium carbonate and guanidinium borate.

11. The bleach powder according to claim 9, wherein alkaline silicate is sodium silicate.

12. The bleach powder according to claim 9, wherein the alkaline metasilicate is sodium metasilicate.

13. The bleach according to claim 9, wherein the trishydroxyalkylamine is trishydroxyethylamine.

14. The bleach powder according to claim 1, wherein the bleach powder further comprises a source of ammonia selected from the group consisting of ammonium halides, diammonium phosphate, ammonium sulfate and mixtures thereof.

15. The bleach powder according to claim 14, wherein the ammonium halide is ammonium chloride.

16. The bleach powder according to claim 14, wherein the ammonia source is a mixture of ammonium chloride and ammonium sulfate.

17. The bleach powder according to claim 1, further comprising at least one hair conditioning agent.

18. The bleach powder according to claim 17, wherein the hair conditioning agent is a monomeric or polymeric compound selected from the group consisting of cationic, anionic, amphoteric and non-ionic compounds.

19. The bleach powder according to claim 18, wherein the hair conditioning agent is polyquaternium-22.

20. The bleach powder according to claim 1, further comprising at least one thickener.

21. The bleach powder according to claim 20, wherein the thickener is hydroxyethylcellulose.

22. The bleach powder according to claim 1, further comprising at least one desiccant.

23. The bleach powder according to claim 22, wherein the desiccant is silica.

24. A substantially dust-free bleach powder, which consists essentially of:

(a) a plurality of particles which comprise a peroxygenated salt;

(b) a substantially hydrophilic de-dusting agent selected from the group consisting of diisopropyl adipate, diisopropyl sebacate, diisopropyl oxalate dimethyl isosorbide, diisopropyl isosorbide, and γ-butyrolactone, wherein the de-dusting agent coats the particles to prevent dust formation;

(c) powdered polytetrafluoroethylene;

(d) a base;

(e) an ammonia source;

(f) a hair conditioning agent;

(g) a thickener; and (h) a desiccant.

25. The bleach powder according to claim 24, wherein the de-dusting agent is present in an amount less than about 10% by weight of the bleach powder.

26. The bleach powder according to claim 24, wherein the de-dusting agent is present in an amount of from about 2 to 50% by weight of the bleach powder.

27. The bleach powder according to claim 24, wherein the de-dusting agent is present in an amount of from about 2 to 3% by weight of the bleach powder.

28. The bleach powder according to claim 24, wherein the powdered polytetrafluoroethylene is present in an amount of about 1–5% by weight of the bleach powder.

29. The bleach powder according to claim 24, wherein the powdered polytetrafluoroethylene is present in an amount of about 2–4% by weight of the bleach powder.

30. The bleach powder according to claim 24, wherein the powdered polytetrafluoroethylene is present in an amount of about 3% by weight of the bleach powder.

31. The bleach powder according to claim 24, wherein the ammonia source is a mixture of ammonium chloride and ammonium sulfate.

* * * * *